(12) United States Patent
Giambattista et al.

(10) Patent No.: US 10,149,939 B2
(45) Date of Patent: Dec. 11, 2018

(54) MEDICAMENT DELIVERY DEVICE

(71) Applicant: SHL Group AB, Nacka Strand (SE)

(72) Inventors: Lucio Giambattista, East hanover, NJ (US); Antonio Bendek, Vernon, NJ (US)

(73) Assignee: SHL Group AB, Nacka Strand (SE)

( * ) Notice: Subject to any disclaimer, the term of this patent is extended or adjusted under 35 U.S.C. 154(b) by 698 days.

(21) Appl. No.: 14/691,706

(22) Filed: Apr. 21, 2015

(65) Prior Publication Data

US 2015/0224259 A1 Aug. 13, 2015

Related U.S. Application Data

(63) Continuation of application No. 13/639,797, filed as application No. PCT/SE2011/050403 on Apr. 5, 2011, now Pat. No. 9,327,083.

(Continued)

(30) Foreign Application Priority Data

Apr. 7, 2010 (SE) .................................. 1050331-6

(51) Int. Cl.
*A61M 5/24* (2006.01)
*A61M 5/32* (2006.01)
*A61M 5/20* (2006.01)
A61M 5/315 (2006.01)
A61M 5/34 (2006.01)

(52) U.S. Cl.
CPC ............ *A61M 5/2448* (2013.01); *A61M 5/20* (2013.01); *A61M 5/3202* (2013.01); *A61M 5/2466* (2013.01); *A61M 5/31553* (2013.01); *A61M 5/31561* (2013.01); A61M 5/347 (2013.01); *A61M 2005/2013* (2013.01); *A61M 2005/2073* (2013.01); *A61M 2205/586* (2013.01)

(58) Field of Classification Search
CPC .... A61M 5/2448; A61M 5/20; A61M 5/2466; A61M 5/31561; A61M 5/347; A61M 5/3202; A61M 5/3204; A61M 2005/2013; A61M 2005/2073; A61M 2205/586; A61M 5/3213; A61M 2005/312; A61M 39/20
USPC .. 604/201, 240–243, 256, 164.08, 192, 198, 604/263
See application file for complete search history.

(56) References Cited

U.S. PATENT DOCUMENTS

2008/0215001 A1\* 9/2008 Cowe .................... A61M 5/326
604/110
2011/0251553 A1\* 10/2011 Ratjen ................. A61M 5/2033
604/89

FOREIGN PATENT DOCUMENTS

GB 2424836 A 11/2006
GB 2451664 A 2/2009
(Continued)

*Primary Examiner* — Kevin C Sirmons
*Assistant Examiner* — Leah Swanson
(74) *Attorney, Agent, or Firm* — McDonnell Boehnen Hulbert & Berghoff LLP

(57) ABSTRACT

Provided is a medicament delivery device (100) comprising a tubular housing (110), having a proximal end (111) and an opposite distal end (112), an actuator means (119, 120), slidably and coaxially arranged inside the tubular housing (110) wherein is provided an inter-locking mechanism (119, 413) between the a cap (410) and the housing (110), enabling the cap (410) to freely spin, i.e. it is impossible to open the cap (410), until the medicament delivery device (100) has been properly activated by an activator means (160).

17 Claims, 13 Drawing Sheets

Related U.S. Application Data

(60) Provisional application No. 61/321,548, filed on Apr. 7, 2010.

(56) References Cited

FOREIGN PATENT DOCUMENTS

| WO | 2005115508 | A1 | 12/2005 |
| WO | 2009150078 | A1 | 12/2009 |

* cited by examiner

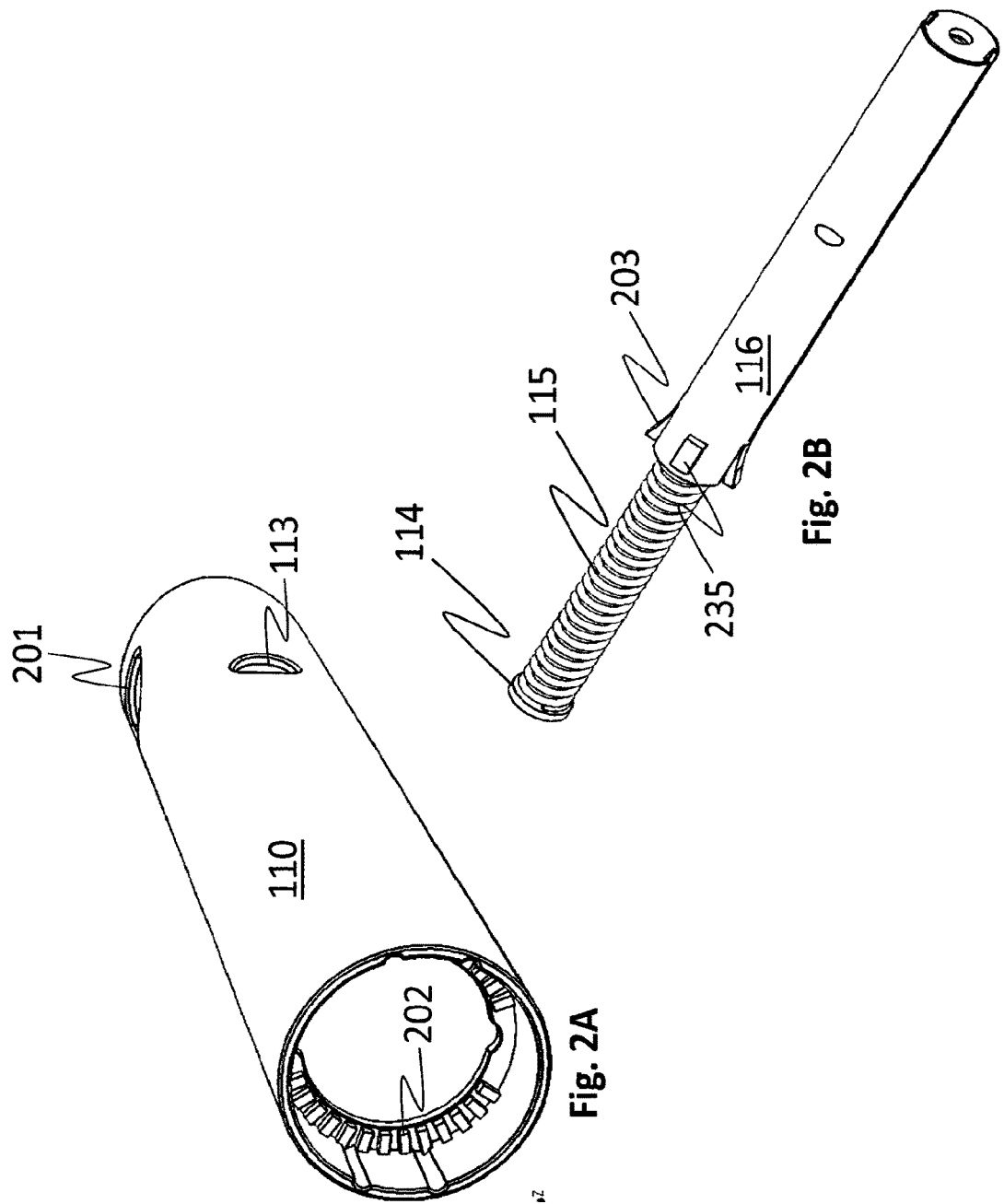

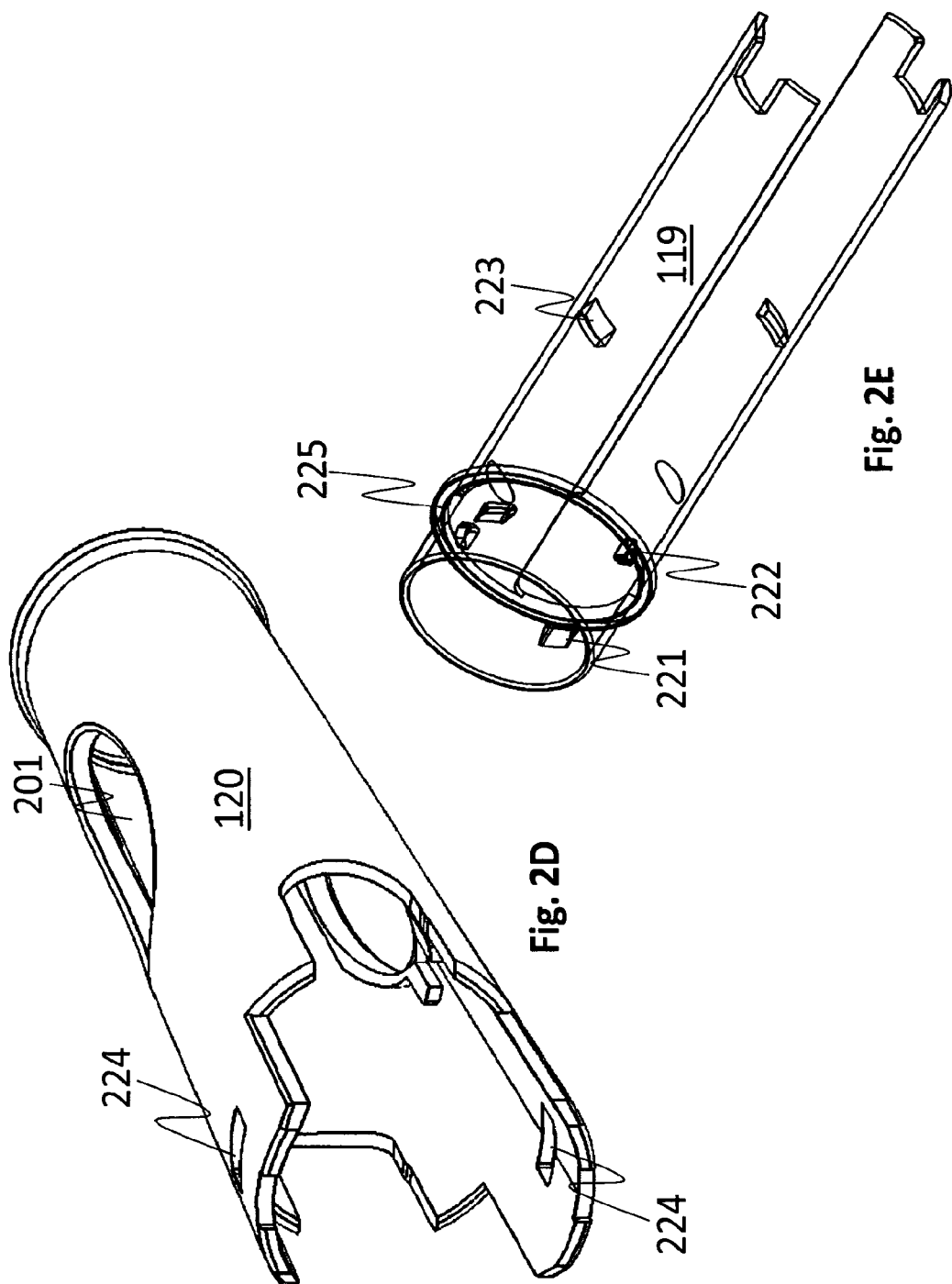

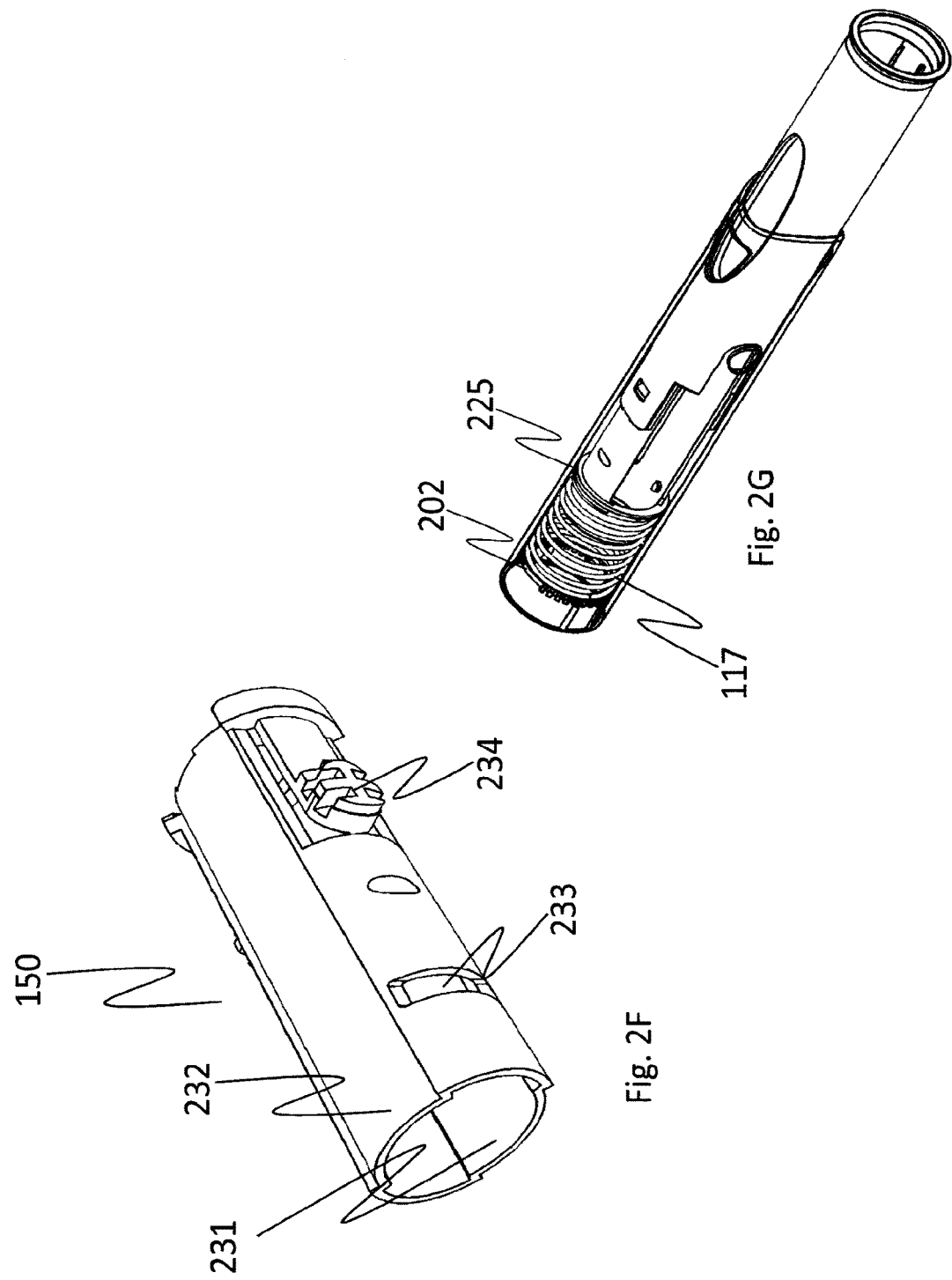

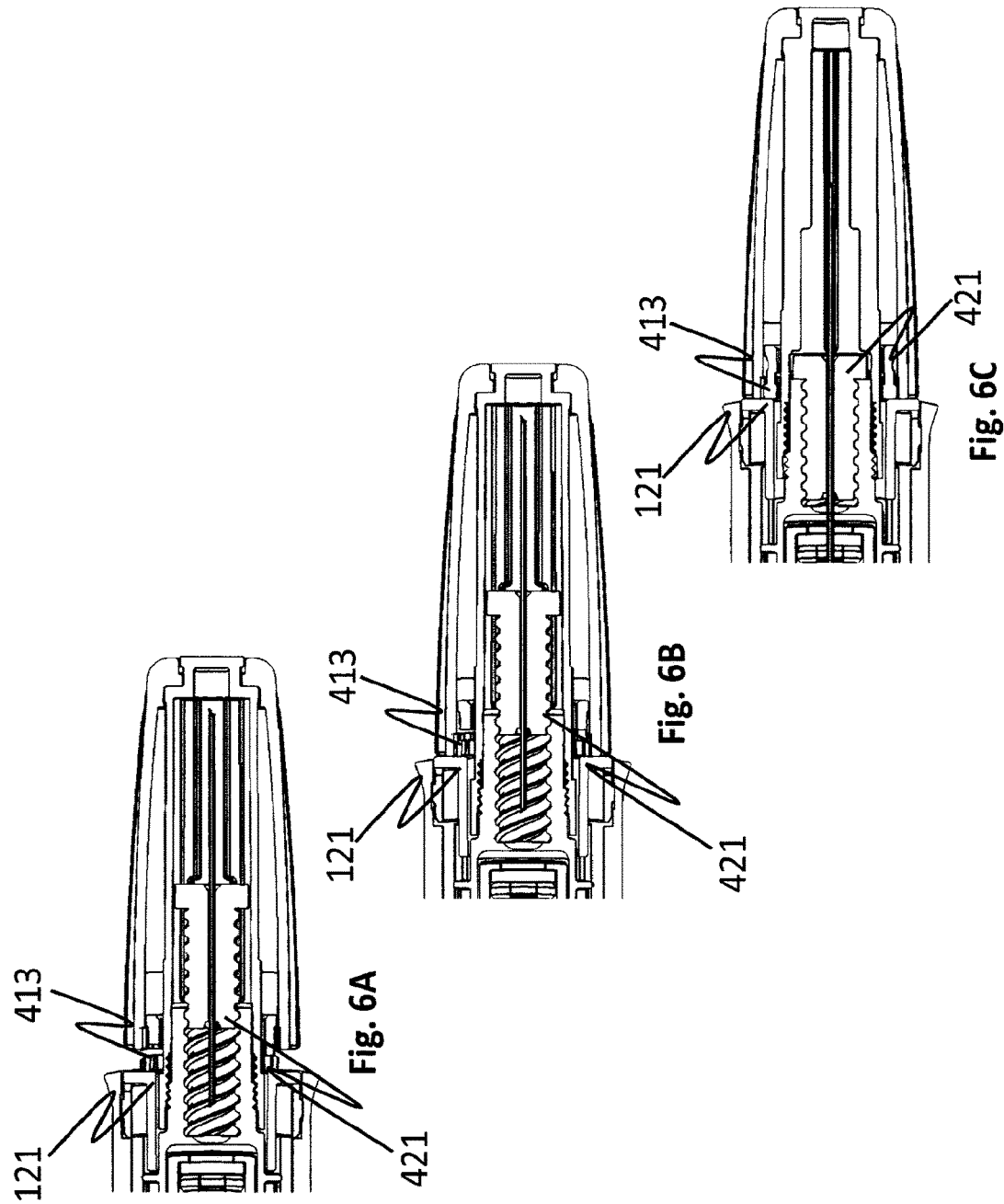

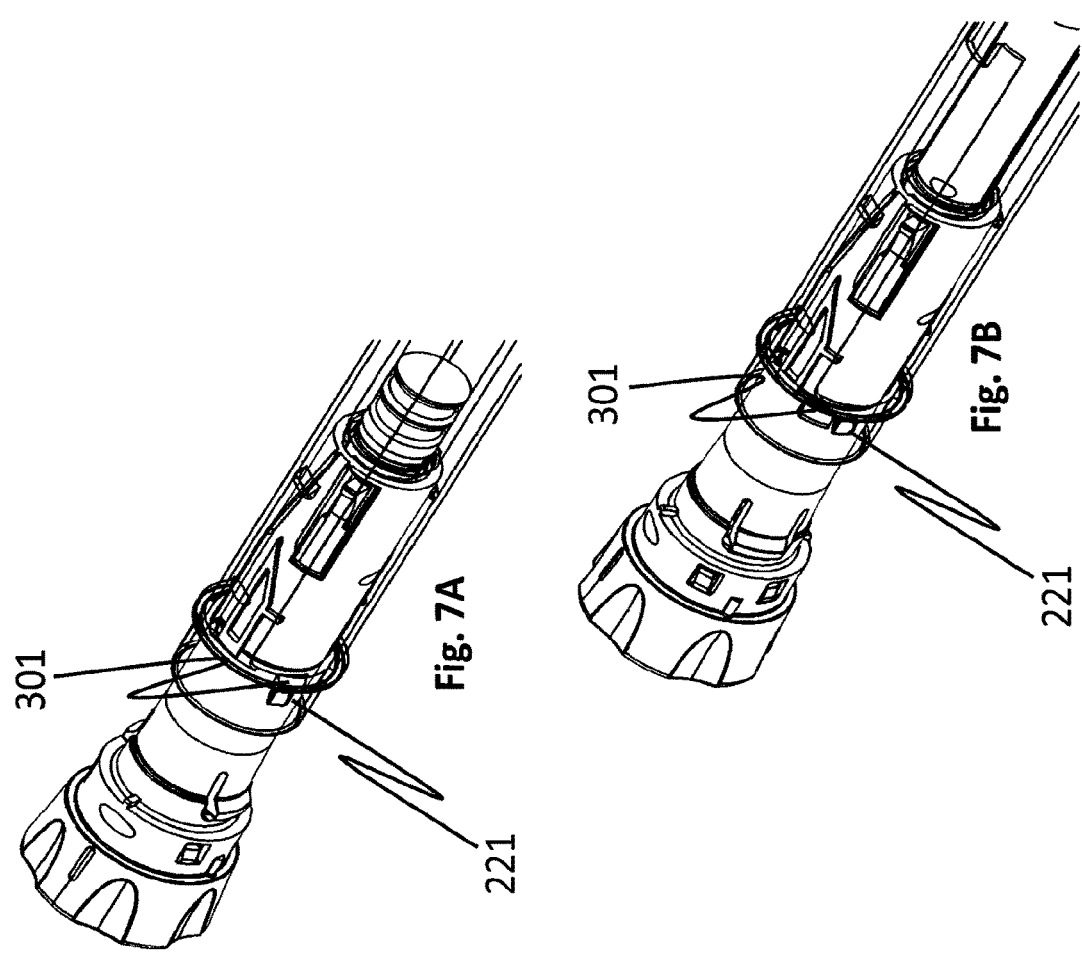

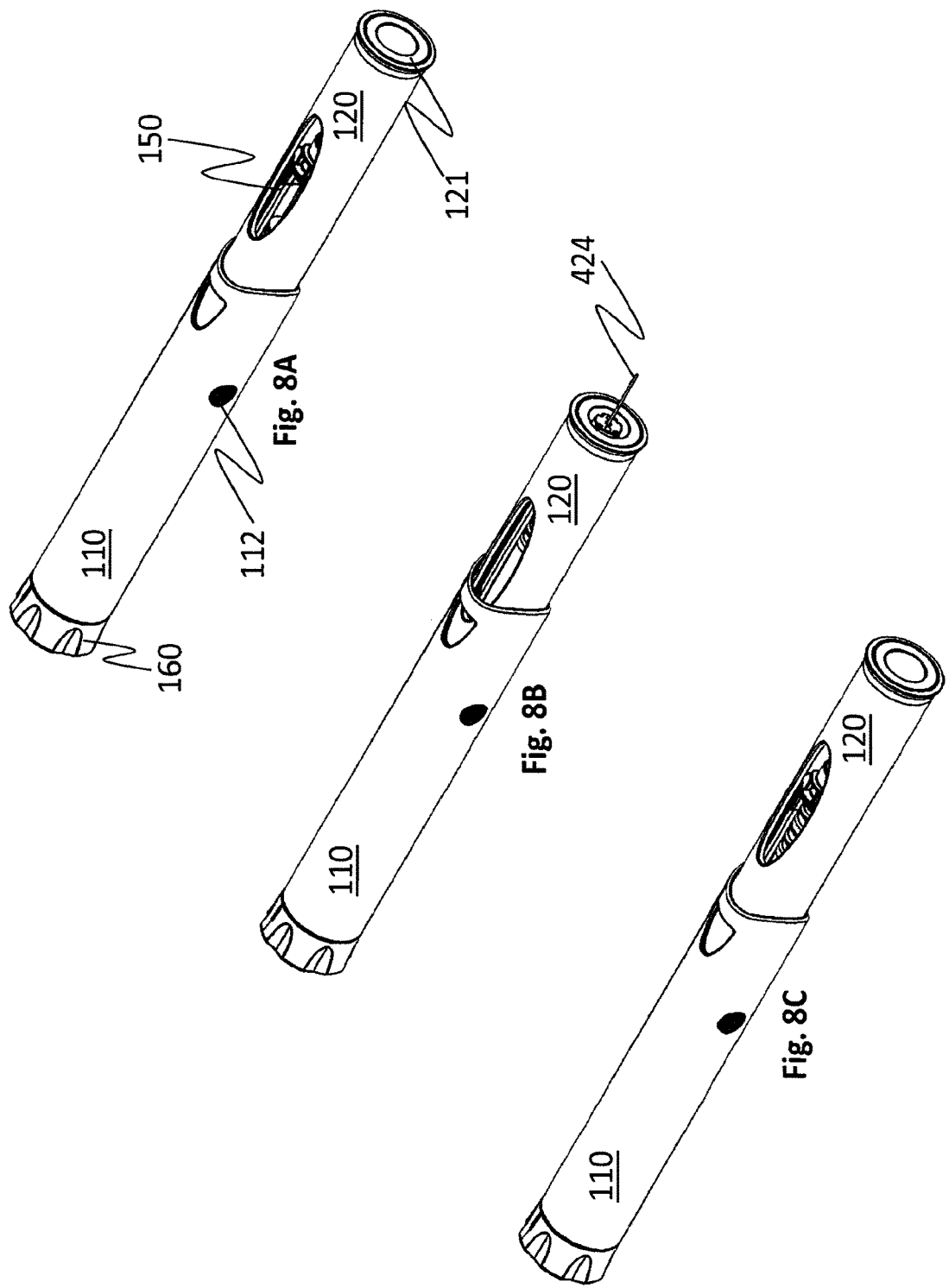

MEDICAMENT DELIVERY DEVICE

CROSS REFERENCE TO RELATED APPLICATIONS

The present application is a continuation application of U.S. patent application Ser. No. 13/639,797, filed Oct. 18, 2012 which is a 371 of International Patent Application No. PCT/SE2011/050403, filed Apr. 5, 2011 which claims the benefit of U.S. Provisional Patent Application No. 61/321, 548, filed Apr. 7, 2010 the entire contents of which are incorporated entirely herein by reference.

TECHNICAL FIELD

The present invention relates to a medicament delivery device and in particular to a medicament injector where safety and handling aspects have been improved by a cap inter-locking arrangement.

BACKGROUND

One solution for keeping a medicament delivery device as pre-assembled as possible is to deliver the medicament delivery device with a delivery member as e.g. a needle; pre-attached. This solution often causes the rear end of the needle to protrude into the interior of the container, which could be a drawback if the medicament reacts with the material of the delivery member when exposed for a period of time. In that respect it would be desirable to have the rear part of the delivery member outside the container until the delivery is to be performed. To minimize the number of actions needed in order to perform the injection, some devices only need to be pressed against the injection area, without the need of injecting by pressing a button or the like, which causes the needle to penetrate the injection area and the device perform the injection. Thereby, the delivery procedure is reduced by at least one step.

One such device is disclosed in patent document EP 1349590 B describing an injector having a number of features that facilitate the handling of the injector. The penetration and injection is performed manually by simply pressing the pressing the proximal end of a needle shield against the delivery area, causing the shield to move in a distal direction, enabling the needle to penetrate the injection area and thereafter initialize the injection process. When the injection is performed the injector is withdrawn whereby a needle shield extracts around the needle in a locked way.

However, a disadvantage of prior art solutions is that they sometimes are unreliable and may unintentionally be actuated, either by mishap or by improper usage. Thus, as can be noted, human handling aspects of the medicament delivery device are crucial and there are several rationales for improving existing solutions. One important safety aspect when handling a medicament delivery device is the locking of the injection actuator, before the medicament delivery device is ready for use. In U.S. Pat. No. 6,893,420 is disclosed a device arranged with a locking means for locking a latch that prevents the automatic penetration and injection means from being released before mixing of the medicament is finished. However this device suffers from the disadvantage of a user having to remove the locking means actively from the device after the mixing is finished, thereby causing an unnecessary step which may be disadvantageous, especially considering emergency usage of said devices. There is therefore a need for an arrangement that can provide improved safety handling, as well as improved medicament handling, i.e. arrangements where the medicament can be in pre-assembled devices but still remain in storage, without having the medicament compromised or degraded due to the medicament reacting with the material of the delivery member when exposed for a period of time and at the same time are both reliable and safe to use at the same time as the medicament delivery device is being intuitive to use.

SUMMARY

An object of the embodiments of the present invention is to provide a medicament delivery device that is both reliable and safe to use and a medicament delivery device that is easy to use when handling. This is achieved by a medicament delivery device comprising a tubular housing, having a proximal end and an opposite distal end, actuator means, slidably and coaxially arranged inside the tubular housing and comprising a proximal annular contact member; a first resilient member arranged at the distal end of the actuator means, between an annular ledge of the tubular housing and an annular ledge of the actuator means; a medicament container holder coaxially arranged within the actuator means and fixedly attached to the tubular housing and further comprising a medicament cartridge having a medicament therein, the medicament cartridge further housing at least one slidable stopper and a membrane; activation means interactively connected to the actuator means and arranged to hold the actuator means and the first resilient member in a pre-tensioned state; drive means, interactively connected either to the actuator means, or to the activation means and to the actuator means for driving the slidable stopper; wherein the medicament delivery device further comprises a delivery member comprising a retainer member fixedly connected to the container holder, a hub coaxially movable within the retainer member and provided with a needle having a proximal and an opposite distal end, an inner cap interactively connected to the hub and to the retainer member, and an outer cap coaxially arranged to the inner cap; wherein said outer cap is rotatably spinning in relation to said inner cap when the actuator means and the first resilient member are in the pre-tensioned state; and a cap inter-locking member axially slidable, but rotationally locked to the inner cap and arranged abutting the proximal annular contact member, and wherein said cap inter-locking member is also arranged to interact with the outer cap when the actuator means and the first resilient member are released from its pre-tensioned state.

According to another aspect of the invention, the actuator means comprises a tubular activation member and an intermediate longitudinal locking member, wherein the proximal annular contact member is coaxially arranged within the inner surface proximal end of the tubular activation member, and wherein the intermediate longitudinal locking member further comprises a first co-acting means interactively connected to a corresponding first co-acting means of the activation means for holding the actuator means and the first resilient member in the pre-tensioned state.

According to yet another aspect of the invention, the first co-acting means is a radial, outward, extending protrusion and the corresponding first co-acting means of the first activation means is a radial inward extending protrusion.

According to a further aspect of the invention, the drive means comprises a tubular operation member having inner co-acting means on its inner surface and outer co-acting means on its outer surface, a plunger rod, a second resilient member pre-tensioned arranged within the plunger rod and a plunger rod support member.

According to yet a further aspect of the invention, the longitudinal tubular inter-locking locking member further comprises a second co-acting means interactively connected to an outer co-acting means of the tubular operation member.

According to another aspect of the invention, the second co-acting means is a radial inward extending protrusion and the outer co-acting means is a groove-track.

According to yet another aspect of the invention, the plunger rod comprises a third co-acting means releasable connected the inner co-acting means of the tubular operation member when the medicament cartridge is a single chamber cartridge, for holding the plunger rod and the second resilient member in a pre-tensioned state, such that when the actuator means is pressed against a delivery site, the tubular operation member is rotated, whereby said plunger rod is released from the actuator means and driven proximally by the force of the second resilient member such that the plunger rod exerts a pressure on the slidable stopper whereby the medicament is expelled through the delivery member.

According to a further aspect of the invention, the plunger rod comprises third co-acting means firstly releasable connected to an inner co-acting means of the activation means and secondly releasably connected to the inner co-acting means of the tubular operation member when the medicament container is a dual chamber cartridge, such that when said activation means is manually operated, the plunger rod is released from the activation means and moves proximally by the force of the second resilient member such that the plunger rod exerts a pressure on the slidable stopper for performing a mixing of medicament, until the third co-acting means abuts the inner co-acting means of the tubular operation member and when the tubular actuator means is pressed against a delivery site, said tubular operation member is rotated, whereby said plunger rod is released from the tubular actuation means and driven proximally by the force of the second resilient member such that the plunger rod exerts a pressure on the slidable stopper and the medicament is expelled through the delivery member.

According to yet a further aspect of the invention, the device further comprises a variable dose a variable dose tubular member fixedly connected to the activation means and rotatable arranged in relation to the tubular operation member.

According to another aspect of the invention, the device further comprises a variable dose tubular member fixedly connected to the activating member and rotatable arranged in relation to the tubular operation member, wherein the variable dose tubular member comprises an inner dose co-acting means.

According to yet another aspect of the invention, the plunger rod comprises additional fourth co-acting means on its outer surface adapted to co-act with the inner co-acting means of the tubular operation member, and wherein the third co-acting means of the plunger rod are releasable with connected to the inner co-acting means of the activation means, such that when said activation means is manually operated, the plunger rod is released from the activation means and moves proximally by the force of the second resilient member such that the plunger rod exerts a pressure on the slidable stopper for performing a mixing of medicament, until the fourth co-acting means abuts the inner co-acting means of the tubular operation member and when the activation means is further manually operated for choosing a preset dose, the variable dose tubular member is also rotated such that a distance between the third co-acting means of the plunger rod and an inner dose co-acting means on the inner surface of the variable dose member determines the size of the dose to be delivered.

According to a further aspect of the invention, the tubular actuator means are adapted to be pressed against a delivery site, such that said tubular operation member is rotated, whereby said fourth co-acting means is released from the inner co-acting means of the tubular operation member allowing the plunger rod to be driven proximally by the force of the second resilient member such that the plunger rod exerts a pressure on the slidable stopper and the set dose of medicament is expelled through the delivery member until the third co-acting means of the plunger rod abuts the inner dose co-acting means on the inner surface of the variable dose member.

According to yet a further aspect of the invention, the cap inter-locking member is an intermediate annular member, having a co-acting means adapted to engage with a corresponding annular co-acting means on the inner sheath of the outer cap, enabling rotation of the outer cap.

By having the medicament delivery device preassembled, without the needle penetrating the membrane at the initial state, unnecessary problems relating to reactions between the medicament and the material of the delivery member, when exposed for a period of time, are avoided. Furthermore, by utilization of a cap inter-locking member, unintentional actuation of the medicament delivery device is completely avoided. This advantage is possible due to the fact that it is impossible to actuate an injection of the medicament contained within the medicament delivery device, without first activating the medicament delivery device. These and other aspects of and advantages with the present invention will become apparent from the following detailed description and from the accompanying drawings.

BRIEF DESCRIPTION OF THE DRAWINGS

In the following description of embodiments of the invention, reference will be made to the accompanying drawings of which:

FIG. 2A is a perspective view of a tubular housing of the medicament delivery device according to the invention.

FIG. 2B is a perspective view of a plunger rod assembly of the medicament delivery device according to the invention.

FIGS. 2D and 2E illustrates the actuator means in a perspective view.

FIG. 2F is a perspective detail view of a medicament container holder.

FIG. 2G is a detail perspective view illustrating a pre-tensioned first resilient member.

FIG. 6A-FIG. 6C illustrates cross-sectional side views of the cap and delivery means assembly in different operating modes.

FIG. 7A-FIG. 7B is perspective illustrations of the activation means in different modes of operation.

FIG. 8A-FIG. 8C illustrates, in perspective, the medicament delivery device in different operating modes.

DETAILED DESCRIPTION

Embodiments of present invention will now be described in detail. As should be noted in present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1A:
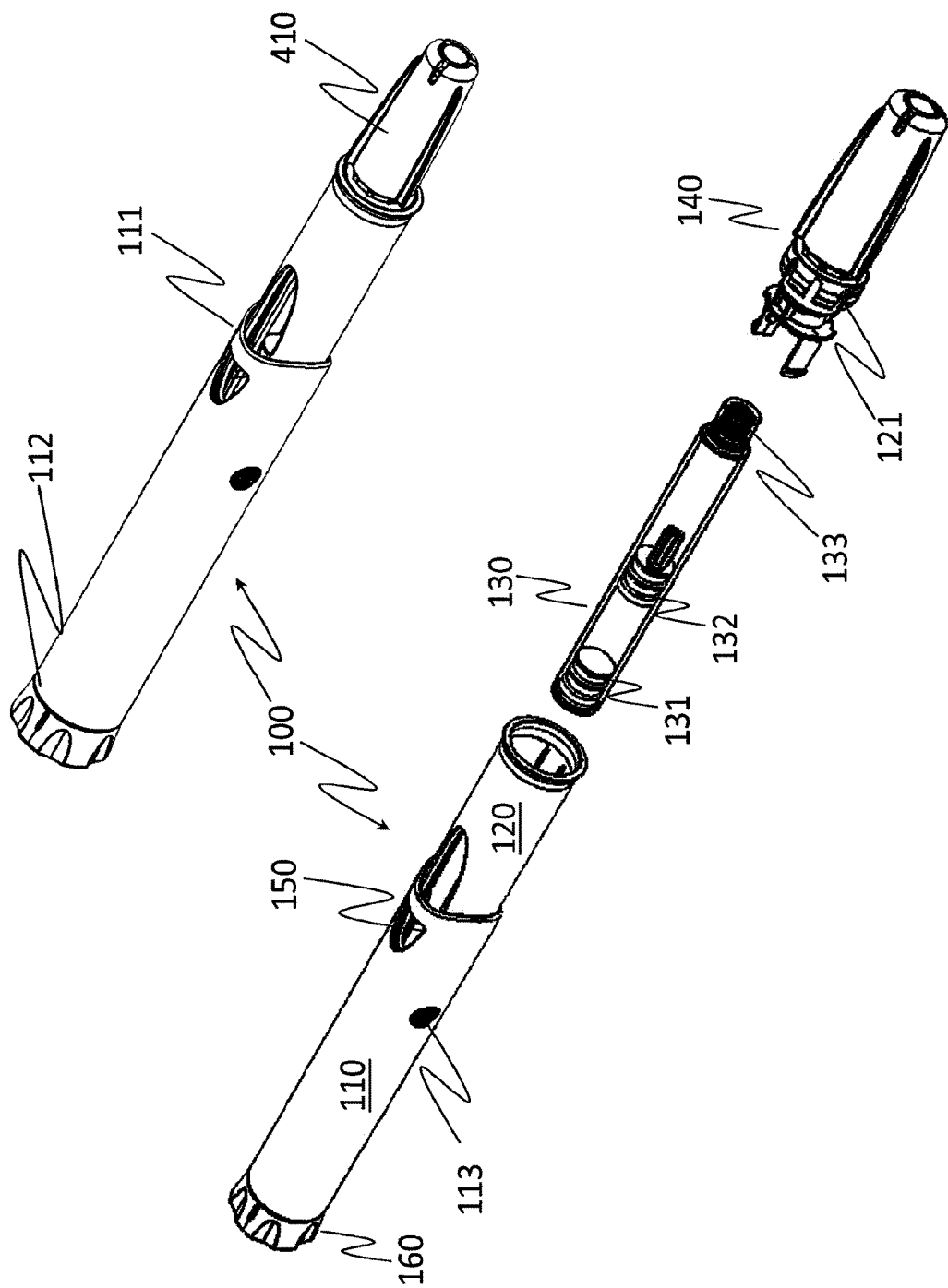
FIG. 1A is a perspective view of a complete medicament delivery device according to the invention.
Figure 1B:
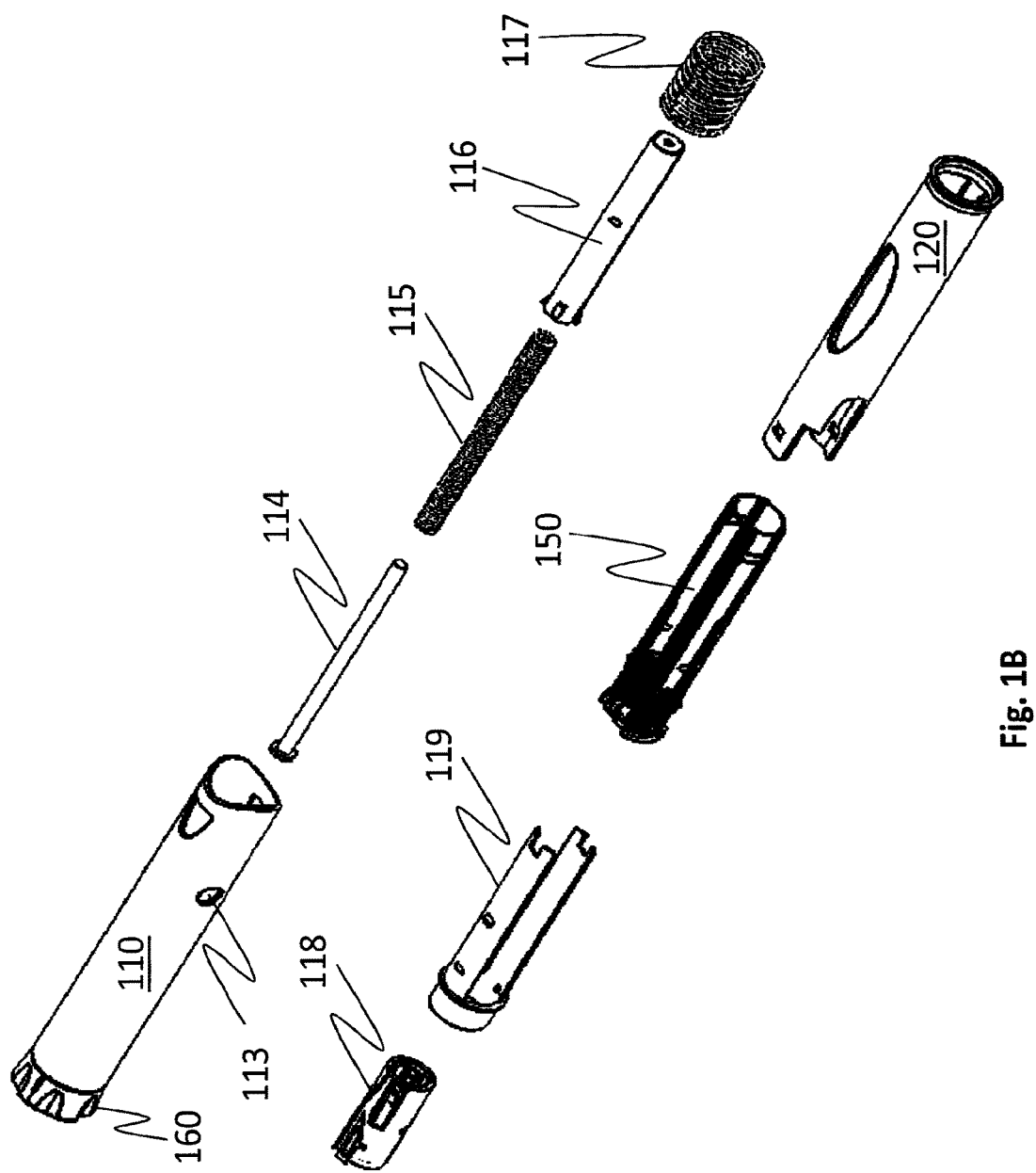
FIG. 1B illustrates an exploded view, comprising exemplary interior components of an exemplary medicament delivery device.

FIG. 1A is a perspective view of a complete medicament delivery device 100 according to the invention and also illustrates a simplified, exploded, perspective view of the medicament injection device 100. In FIG. 1A is illustrated an initial, non-activated, state of the pre-assembled medicament injection device 100 having an outer cap 410 mounted thereon. The medicament delivery device 100 further comprises a tubular housing 110, having a proximal end 111 and an opposite distal end 112, actuator means comprising a tubular activation member 120, slidably and coaxially arranged inside the tubular housing 110, an intermediate longitudinal locking member 119 and a proximal annular contact member 121. The medicament delivery device 100 also comprises a first resilient member 117 (see FIG. 1B) arranged at the distal end of the actuator means, between an annular ledge 202 of the tubular housing 110 and an annular ledge 235 of the intermediate longitudinal locking member 119 for moving the actuator means in a proximal direction. The medicament delivery device 100 furthermore comprises a medicament container holder 150 which is coaxially arranged within the tubular actuator member 120 and fixedly attached to the tubular housing 110 via radial extensions 234 (see FIG. 2F) protruding through corresponding openings 113 in the tubular housing 110. Included in the medicament delivery device 100 is also a medicament container 130, which is arranged within the medicament container holder 150 and further housing at least one slidable stopper 131, 132. In an exemplary embodiment of the invention, the medicament container is a cartridge having a membrane 133. The medicament delivery device 100 further comprises drive means comprising a tubular operation member 118 having inner co-acting means on its inner surface and outer co-acting means on its outer surface, a plunger rod 116, a second resilient member 115 pre-tensioned arranged within the plunger rod and a plunger rod support member 114 (see FIG. 1B). The medicament delivery device 100 further comprising activation means hereinto fore named as an activating member 160 arranged at the distal end of the tubular housing 110 and is used for activating the medicament delivery device 100, i.e. to make the medicament delivery device ready for use. The activating member 160 is, in an exemplary embodiment of the invention, a knob which is rotatable around an axis extending from the distal-to-the proximal end of the medicament delivery device 100. In a preferred embodiment of the invention, the tubular operation member 118 is rotatable arranged between the container holder 150 and the activating member 160. The medicament delivery device 100 furthermore comprises a delivery member 140.

Figure 2C:
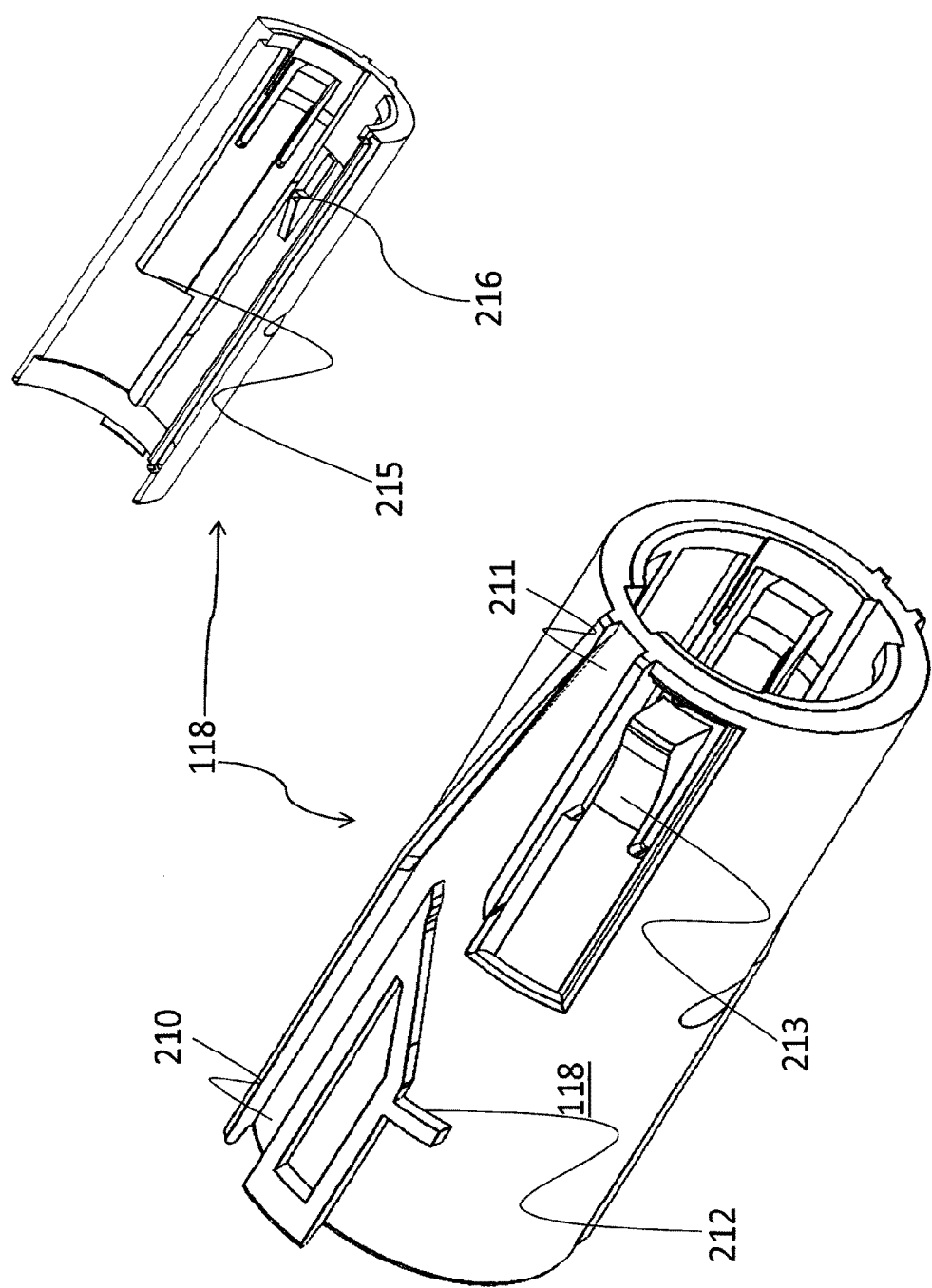
FIG. 2C is a perspective view of an exemplary tubular operation member of the medicament delivery device.

FIG. 2A shows a perspective detail view of the tubular housing 110 having the corresponding opening 113 for receiving the radial extensions 234 (see FIG. 2C) for fixedly attaching the medicament container holder 150 to the tubular housing 110. FIG. 2A further illustrates a second opening 201, enabling a user to view the injection process. Also disclosed in FIG. 2A is the annular ledge 202, for supporting the first resilient member 117 in a pre-tensioned state, between the tubular housing 110 and the intermediate longitudinal locking member 119.

FIG. 2B illustrates, in perspective, a plunger rod assembly in a more detailed view. The plunger rod assembly comprising the plunger rod support member 114, the second resilient member 115 and the plunger rod 116. On the outer radial surface of the plunger rod 116 is provided with third co-acting means as e.g. protrusions 235, adapted to co-act with an inner co-acting means as a ledge 236 of the activating member 160, in order to keep the plunger rod 116 in a pre-tensioned, un-activated state.

FIG. 2C illustrates a detail perspective view of the tubular operation member 118. The tubular operation member 118 comprises outer co-acting means as e.g. at least one groove 210, 211, 212 on an outer surface of the tubular operation member 118, arranged such that a second co-acting means as e.g. a radial inward extending protrusion 222 of the intermediate longitudinal locking actuator 119 is adapted to be guided within the at least one groove 210, 211, 212 forcing the tubular operation member 108 to rotate when the intermediate longitudinal locking actuator 119 is axially moved, as a result of the axial movement of the inter-connected tubular actuator member 120. In a further embodiment, the medicament delivery device 100 comprises a locking means, interactively connected to the intermediate longitudinal locking member 119 and thus also to the tubular activation member 120. The locking means is preferably a flexible tongue 213 arranged on the tubular operation member 118. The flexible tongue 213 is arranged to lock the second co-acting means as e.g. the radial inward extending protrusion 222 of the intermediate longitudinal locking actuator 119 when the actuator means has been completely extended towards the proximal direction. FIG. 2C shows also a radial inwardly extending protrusion 216 on the inner surface of the tubular operation member is arranged to lock a radial outward extending flexible protrusion 203 on the distal end of the plunger rod 116, when the plunger rod 116 passes through the interior of the tubular operation member 118; i.e. when the plunger rod 116 is moved in a proximal direction. FIG. 2C also illustrates in cross-sectional perspective view of an inner co-acting means 215 of the tubular operation member 118. The inner co-acting means 215 comprising a ledge and a groove.

In an exemplary embodiment of the invention, when the medicament cartridge 130 is a single chamber cartridge, the third co-acting means 235 of the plunger rod 116 are releasable connected the inner co-acting means 215 of the tubular operation member 118 for holding the plunger rod 116 and the second resilient member 115 in a pre-tensioned state, such that when the actuator means 119,120 is pressed against a delivery site, the tubular operation member 118 is rotated, whereby said third co-acting means 235 is released from the inner co-acting means 215 of the tubular operation member 118 and the plunger rod is driven proximally by the force of the second resilient member 115 such that the plunger rod 116 exerts a pressure on the slidable stopper 131 whereby the medicament is expelled through the delivery member 140.

In yet an exemplary embodiment of the invention, the plunger rod 116 of the medicament delivery device 100 comprises a third co-acting means 235 which firstly is releasable connected to an inner co-acting means 236 of the activation means 160 and secondly releasable connected to the inner co-acting means 215 of the tubular operation member 118, when the medicament container 130 is a dual chamber cartridge, such that when said activation means 160 is manually operated, the plunger rod 116 is released from the activation means 160 and moves proximally by the force of the second resilient member 115 such that the plunger rod 116 exerts a pressure on the slidable stopper 131, 132 for performing a mixing of medicament, until the third co-acting means 235 abuts the inner co-acting means 215 of the tubular operation member 118 and when the tubular actuator means 119,120 is pressed against a delivery site, said tubular operation member 118 is rotated, whereby said third co-acting means 235 is released from the inner co-acting means 215 of the tubular operation member 118 and the plunge rod is driven proximally by the force of the second resilient member 115 such that the plunger rod 116 exerts a pressure on the slidable stopper 131,132 and the medicament is expelled through the delivery member 140.

In an alternative embodiment of the invention, a variable dose tubular member (not shown) is fixedly connected to the activating member 160 and rotatable arranged in relation to the tubular operation member 118. The variable dose tubular member comprises inner dose co-acting means formed as step ledges. Further, the plunger rod 116 comprises additional fourth co-acting means on its outer surface. When the medicament container 130 is a dual chamber cartridge, the third co-acting means 235 of the plunger rod 116 are releasable connected to the inner co-acting means 236 of the activation means 160, such that when said activation means 160 is manually operated, the plunger rod 116 is released from the activation means 160 and moves proximally by the force of the second resilient member 115 such that the plunger rod 116 exerts a pressure on the slidable stopper 131, 132 for performing a mixing of medicament, until the fourth co-acting means abuts the inner co-acting means 215 of the tubular operation member 118. When the activation means 160 is further manually operated for choosing a preset dose, the variable dose tubular member is also rotated such that a distance between the third co-acting means 235 of the plunger rod 116 and a step ledge on the inner surface of the variable dose member determines the size of the dose to be delivered. When the tubular actuator means 119,120 is pressed against a delivery site, said tubular operation member 118 is rotated, whereby said fourth co-acting means is released from the inner co-acting means 215 of the tubular operation member 118 and the plunger rod 116 is driven proximally by the force of the second resilient member 115 such that the plunger rod 116 exerts a pressure on the slidable stopper 131,132 and the set dose of medicament is expelled through the delivery member 140, until the third co-acting means 235 of the plunger rod 116 abuts the step ledge on the inner surface of the variable dose member.

FIG. 2D illustrates the tubular actuator member 120 in a perspective view. The tubular actuator member 120 comprises a recess or an opening 224 arranged to receive a corresponding protrusion 223 of the intermediate longitudinal locking member 119 for fixedly attaching the intermediate longitudinal locking member 119 to the tubular actuator member 120. The tubular actuator member 120 further comprises an annular contact member 121 arranged for pressing against the skin of a patient, and an opening 201 arranged for viewing the medicament delivery process.

FIG. 2E is a perspective view of the intermediate longitudinal locking member 119. The intermediate longitudinal locking member 119 comprises a first co-acting means 221 adapted to co-act with a corresponding co-acting means 301 of the activating member 160 for holding the actuator means and the first resilient member in a pre-tensioned state. In an exemplary embodiment the first co-acting means 221 of the intermediate longitudinal locking member 119 is a protrusion on the outer, distal annular wall of the intermediate longitudinal locking member 119 and the corresponding first co-acting means 301 is a radial inward extending protrusion.

FIG. 2F is a perspective detail view of the medicament container holder 150 showing an opening 233, in an exemplary embodiment of the invention there is a corresponding opening 233 on the other side of the medicament container holder 150 (not illustrated). The medicament container holder 150 further comprises a radial extension 234 for fixedly attaching the medicament container holder 150 to the tubular housing 110 via the corresponding opening 113 (see FIG. 2A). In an exemplary embodiment of the invention there are two radial extensions 234 for fixedly attaching the medicament container holder 150 to the tubular housing 110 via the two corresponding openings 113. The medicament container holder 150 further having an opening 233 for mating with a corresponding support means of the delivery member (see FIG. 4A) and the medicament container holder 150 also has a predefined profile 231, 232 for fixating in a corresponding profile of the intermediate longitudinal locking member 119.

FIG. 2G illustrates in perspective the first resilient member 117 being interactively connected, in a pre-tensioned state, to an annular co-acting means 202 of the tubular housing 110 and to a corresponding co-acting means 225 of the intermediate longitudinal locking member 119.

Figure 3B:
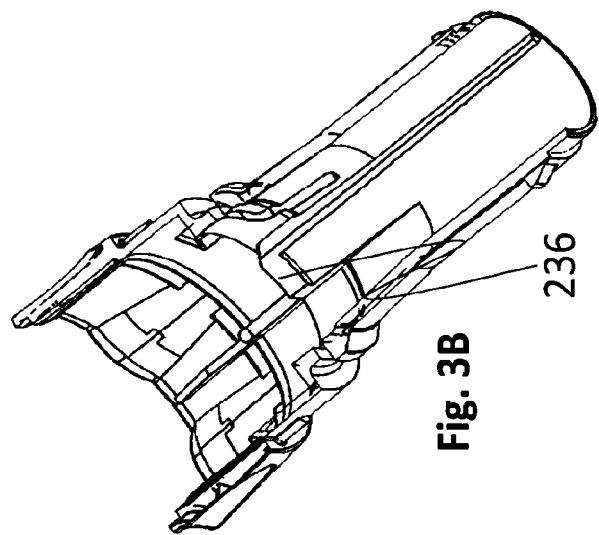
FIG. 3B is a cross-sectional perspective view of the activation means.
Figure 3A:
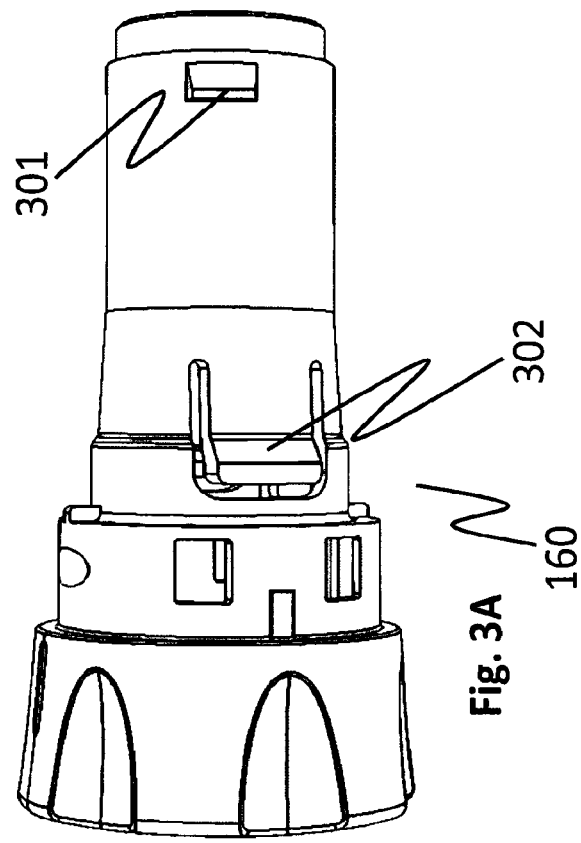
FIG. 3A illustrates a side view of the activation means of the medicament delivery device according to the invention.

FIG. 3A illustrates a side view of the activating member 160. Said activating member 160 has a fixating means 302, i.e. a flexible tongue, for attaching the activating member 160 to a corresponding fixating means at the distal end of the tubular housing 110. The activating member 160 further comprises a first co-acting means 301 for interactively connecting the activating member 160 to a corresponding co-acting means 221 of the intermediate longitudinal locking member 119. In an exemplary embodiment of the invention, the first co-acting means 301 is a protrusion and the corresponding co-acting means 221 of the intermediate longitudinal locking member 119 is also a protrusion.

FIG. 3B is a cross-sectional perspective view of the activating member 160 showing the inner co-acting means as a ledge 236 arranged to co-act with the corresponding third co-acting means 235 of the plunger rod 116 in order to keep the plunger rod assembly in a pre-tensioned state.

Figure 4A:
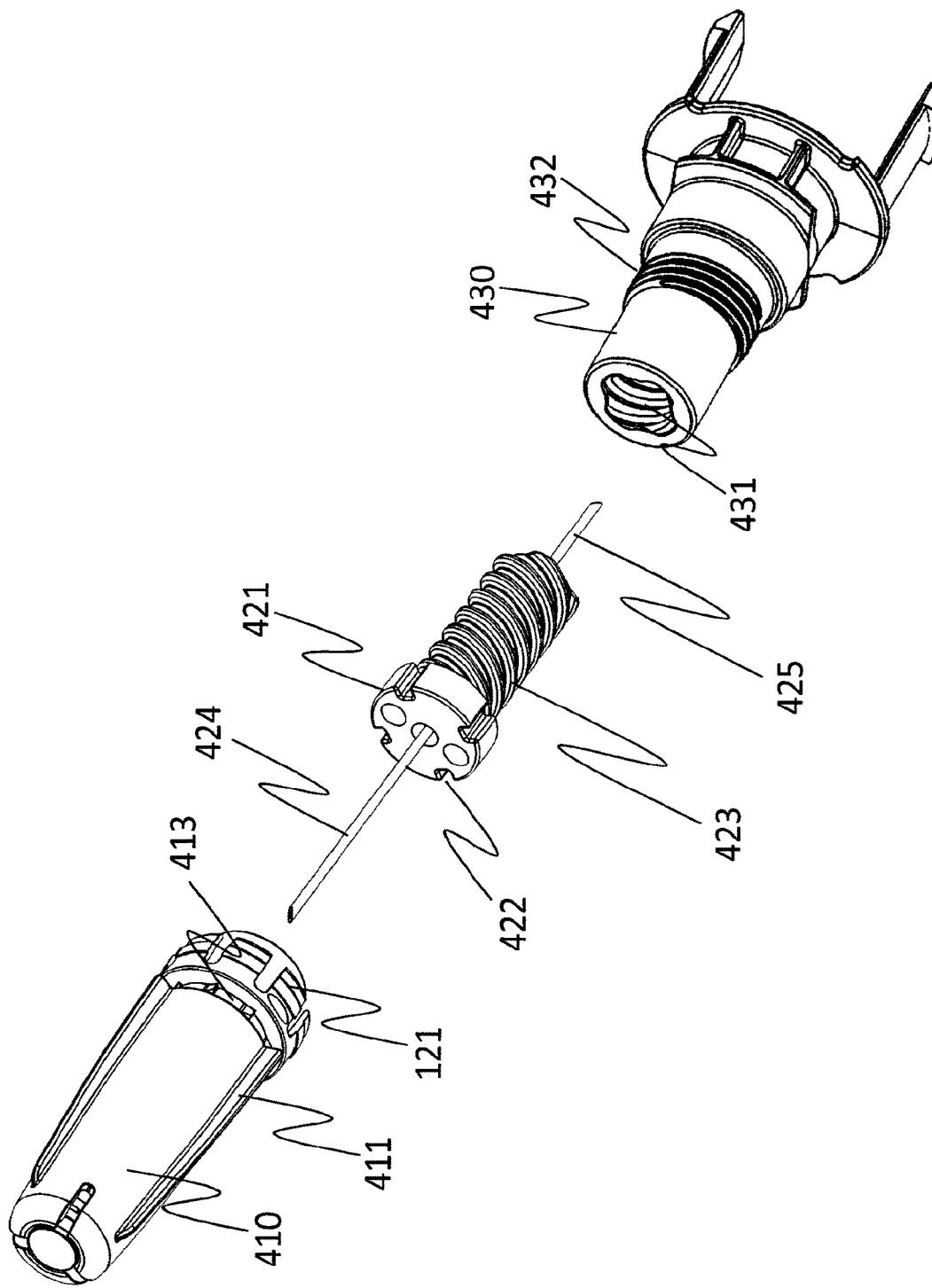
FIG. 4A shows a perspective view of a delivery means assembly of the medicament delivery device according to the invention.

FIG. 4A shows a perspective view of the deliver member 140 comprising a retainer member 430 which is fixedly connected to the medicament container holder 150, a hub 421 where the hub 421, provided with a needle having a proximal 424 and an opposite distal end 425, comprises a first coupling means 423, e.g. in the form of threads on an outer surface of the hub 421, adapted to be interactively connected to a corresponding first coupling means 431 of the retainer member 430; an inner cap 416 interactively connected to the hub and to the retainer member; an outer cap 410 coaxially arranged to the inner cap, wherein said outer cap is rotatably spinning in relation to said inner cap when the actuator means and the first resilient member are in the pre-tensioned state; and a cap inter-locking member 413 axially slidable, but rotationally locked to the inner cap (416) and arranged abutting the proximal annular contact member 121, and wherein said cap inter-locking member is also arranged to interact with the outer cap when the actuator means and the first resilient member are released from its pre-tensioned state. The hub 421 also comprises a second coupling means 422, e.g. in the shape of radial recesses in the proximal end of the hub 421, interactively connected to a corresponding second coupling means 415 (see FIG. 4B), e.g. in the shape of radial inward extensions, of the inner cap 416. In the drawings the numbers of second coupling means 415, 422 are four. However, the number of coupling means 415, 422 is optional as long the intentional function is achieved, i.e. to transfer a rotational movement from the inner cap 416 to the hub 421 and at the same time allowing the hub 421 to move in the distal direction. The hub 421 is arranged and being coaxially movable within the retainer member 430. Upon movement of the hub 421 in the distal direction the distal needle end 425 will penetrate the membrane 133. The cap inter-locking member 413 is an intermediate annular member, having a co-acting means adapted to engage with a corresponding annular co-acting means 417 on the inner sheath of the outer cap, enabling rotation of the outer cap.

Figure 4B:
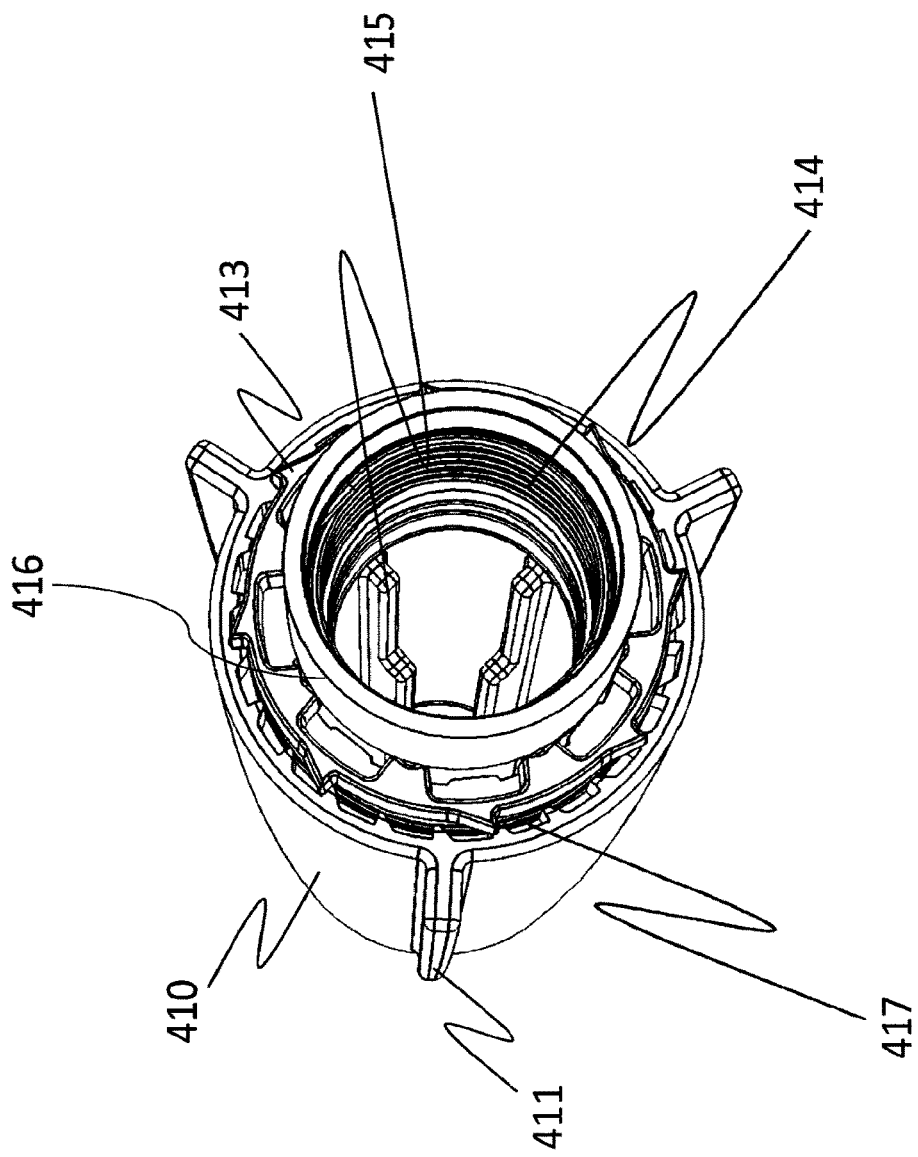
FIG. 4B is a perspective view of an outer cap, a cap inter-locking member and an inner cap seen from its distal end.

FIG. 4B is a perspective view of the outer cap 410 seen from its distal end. The outer cap 410 comprises on its outer surface one or many radial outward extending turning members 411, preferably two, three or four wing-like members, provided for enabling a user-friendly and easy grip of the outer cap 410 when turning off the outer cap 410. As an alternative, the outer cap 410 may be provided with an increased cross-sectional diameter in the section of the outer cap 410 arranged proximally to the tubular actuator member 120 when the cap 410 is attached to the medicament delivery device 100. Also in FIG. 4B is seen the inner cap 416 having a third coupling means 414, e.g. in the shape of internal threads, interactively connected to corresponding third coupling means 432 of the retainer member 430 (see FIG. 4A). The third coupling means 414 is arranged at the inner surface of a distally directed outer sheath of the inner cap 416 having a circular cylindrical shape. It is, however, to be noticed that the threads 414, 432 between the inner side of the inner cap 416 and outer surface of the retainer member 430, has a different direction of the pitch than the threads 423, 431 between the hub 421 and the inner surface of the retainer member 431. When the user then starts to turn the outer cap 410, when engaged to the inner cap by the cap interlocking member, this turning causes the hub 421 to be screwed into the retainer member 430 whereby the pointed distal end 425 of the injection needle penetrates the membrane 133 of the medicament container 130 and due to the different direction of the pitch, the inner cap 416 is screwed off and thereby the outer cap and the inner cap may be removed. Preferably, the pitches of the threads are chosen such that there is a major longitudinal movement of the hub 421 in the distal direction for a small turning angle in order to prevent as much as possible turning or "drilling" of the distal end 425 of the injection needle in the membrane 133. At the same time the pitch of the threads between the cap 410 and the retainer member 430 is preferably chosen such that the user only needs to turn the cap 410 about half a turn in order to perform the operation, so as to avoid having to change grip in order to finish the operation. In FIG. 4B is further illustrated the cap inter-locking member 413 for locking the outer cap 410 to the inner cap 416. When the cap inter-locking member 413 is in its un-locked position, the outer cap 410 is rotatably spinning in relation to said inner cap, i.e. it is impossible to remove the outer cap 410. Thus it is not possible to use the medicament delivery device 100 when the cap inter-locking member 413 is in its un-locked position. When the activating member 160 is rotated, a protrusion 221 on the outer annular wall of the intermediate longitudinal inter-locking actuator 119 is released from the co-operating protrusion 301 of the activating member 160 (see FIG. 7A and FIG. 7B) and the actuator means are forced in a proximal direction, by the force exerted by the first resilient member 117, whereby the annular contact member 121 which is in contact with the cap inter-locking member 413 pushes the cap inter-locking member 413 proximally, such that the outer cap is locked to the inner cap, which is a locked position of the cap inter-locking member 413 (see FIG. 6A to FIG. 6C).

Figure 5:
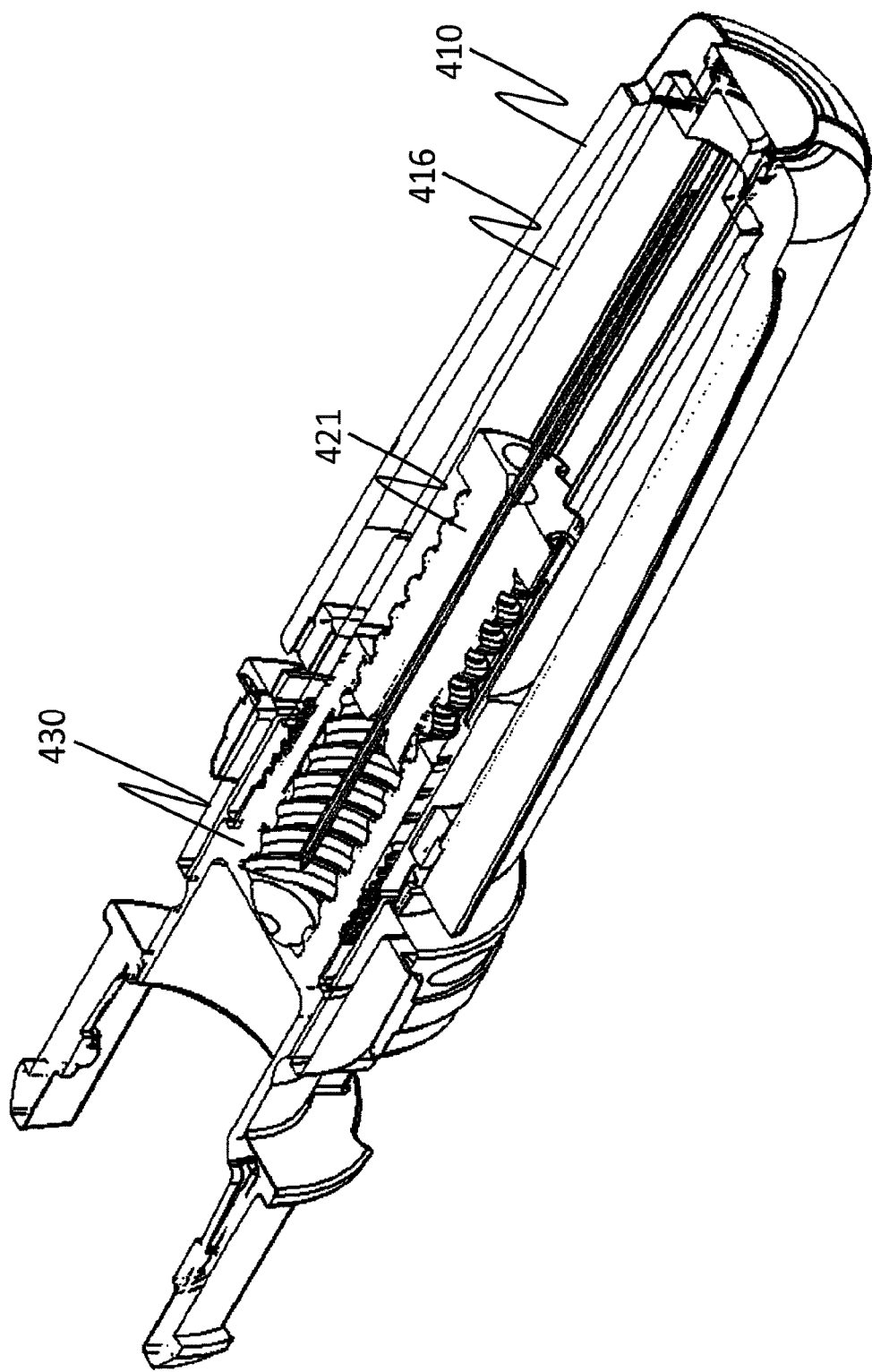
FIG. 5 is a cross-sectional perspective view of the delivery means.

FIG. 5 is a cross-sectional perspective view of the delivery assembly showing the retainer member 430 which is fixedly connected to the medicament container holder 150, the outer cap 410, the inner cap 416 and the hub 421.

FIG. 6A illustrates a cross-sectional side view of the outer cap 410 and the retainer member 430 assembly in an initial mode; wherein the cap inter-locking member 413 is in an un-locked position.

FIG. 6B illustrates the same cross-sectional side view of the outer cap 410 and the retainer member 430 assembly in a 'mixed' or 'ready' mode wherein the cap inter-locking member 413 is pushed axially in a proximal direction by the actuator means to a locked position.

FIG. 6C again illustrates the same cross-sectional side view of the outer cap 410 and retainer member 430 assembly in a 'primed' mode wherein the cap inter-locking member 413 remains in the locked position and where outer cap 410 is being removed causing the hub 421 to move axially in a distal direction, forcing the distal needle end 425 to penetrate the membrane 133 of the medicament container 130.

FIG. 7A is a perspective illustration of the activating member 160 in an initial, un-activated state, interactively connected to the intermediate longitudinal locking member 119. In the initial state the first co-acting means of the intermediate longitudinal locking member 119 is engaged to the corresponding first co-acting means of the activating member 160.

FIG. 7B is a perspective illustration of the activating member 160 in a second, activated state, interactively connected to the intermediate longitudinal locking member 119. In the second state, the first co-acting means of the intermediate longitudinal locking member 119 is released from its engagement to the corresponding first co-acting means of the activating member 160.

FIG. 8A to FIG. 8C illustrates, in perspective, the medicament delivery device 100 from its activated state, shown in FIG. 8A, wherein the distal needle end 425 (see also FIG. 4A) has penetrated the membrane 133 (FIG. 1A) and the medicament delivery device 100 is in a ready-to-use state, via FIG. 8B, wherein is illustrated the actual injection state, showing a proximal needle end 424 ready to expel the medicament and finally in FIG. 8C is shown a locked state of the medicament delivery device 100, i.e. injection has been made. When the medicament delivery device 100 is ready for use the user is about to make an injection he/she presses the proximal end, i.e. the annular contact member 121, against the skin. The tubular actuator member 120 is then moved in a distal direction in relation to the tubular housing 110 and during the relative movement the proximal needle end 425 manually penetrates the skin. When the tubular actuator member 120 is about to reach the most distal position, in relation to the tubular housing 110, the injection is made; i.e. when the tubular actuator member 120 passes by a predetermined injection position, close to its most distal position, the injection state is achieved. This penetration and injection state is shown in FIG. 8A-FIG. 8C. When the injection is made, the user removes the medicament delivery device 100 from the skin, thereby allowing the tubular actuator member 120 to move in a proximal direction in relation to the tubular housing 110 by a force exerted by the first resilient member 117 and finally reaches its final state; i.e. the locked state. In the locked state, the tubular actuator member 120 once more is in its most proximal position as illustrated by FIG. 8C. In this state, the proximal part of the tubular actuator member 120 fully protects the proximal needle end 424 and the tubular actuator member 120 is also locked in that position, in order to prevent unintentional availability of the proximal needle end 424. Thus, for activating the medicament delivery device 100 a user has to press the annular contact member 121, against the skin, this will by inter-engaging means, release the plunger rod 116 in a proximal direction in relation to the tubular housing 110, exerted by force of the second resilient means 115. The plunger rod will thus force the slidable stopper 131, 132 to also move in a proximal direction in relation to the tubular housing 110 and allowing the medicament to be expelled.

Embodiments described herein prevent a user from, unintentionally, activating the medicament delivery device 100 without first having mixed the medicament in the medicament container 130.

The present invention is not limited to the above-described preferred embodiments. Various alternatives, modifications and equivalents may be used. Therefore, the above embodiments should not be taken as limiting the scope of the invention, which is defined by the appended claims.

The invention claimed is:

1. A medicament delivery device comprising:
   a delivery member comprising:
      a retainer member coupled to a hub via a first coupling;
      a needle fixedly connected to the hub and comprising a distal needle end and a proximal needle end;
      an inner cap coupled to the hub via a second coupling and coupled to the retainer member via a third coupling;
      an outer cap coaxially arranged to the inner cap; and
      a cap inter-locking member axially slidable and rotationally locked to the inner cap,
      wherein the cap inter-locking member is configured to engage with an annular member on an inner surface of the outer cap.

2. The medicament delivery device of claim 1 wherein the cap inter-locking member is configured to engage the annular member on the inner surface of the outer cap so as to enable rotation of the outer cap in relation to the inner cap.

3. The medicament delivery device of claim 1 wherein the cap inter-locking member is configured to engage the annular member on the inner surface of the outer cap to rotationally lock the outer cap to the inner cap.

4. The medicament delivery device of claim 1 wherein the retainer member is coupled to a medicament container.

5. The medicament delivery device of claim 1 wherein the hub is configured to move coaxially within the retainer member.

6. The medicament delivery device of claim 1 wherein upon movement of the hub in the distal direction, the distal needle end is configured to penetrate a membrane of a medicament container.

7. The medicament delivery device of claim 1, wherein the outer cap and inner cap are removable after being rotationally locked.

8. The medicament delivery device of claim 1, wherein the outer cap and inner cap are removable after the distal needle end has penetrated the membrane.

9. A medicament delivery device comprising:
   a tubular housing coupled to a tubular activation member;
   a medicament container holder coupled to the tubular activation member; and
   a delivery member coupled to the medicament container holder, the delivery member comprising:
      a retainer member coupled to a hub via a first coupling;
      a needle fixedly connected to the hub and comprising a distal needle end and a proximal needle end;
      an inner cap coupled to the hub via a second coupling and coupled to the retainer member via a third coupling;
      an outer cap coaxially arranged to the inner cap; and
      a cap inter-locking member axially slidable and rotationally locked to the inner cap,
      wherein the cap inter-locking member is configured to engage an annular member on an inner surface of the outer cap to either enable rotation of the outer cap in relation to the inner cap or rotationally lock the outer cap to the inner cap; and
   wherein the retainer member is coupled to the medicament container holder;
   wherein the hub is configured to move coaxially within the retainer member; and
   wherein upon movement of the hub in the distal direction, the distal needle end is configured to penetrate a membrane of a medicament container contained within the medicament container holder.

10. The medicament delivery device of claim 9, wherein the first coupling comprises a first thread, having a first pitch, on an outer surface of the hub and a corresponding second thread, having the first pitch, on an inner surface of the retainer member.

11. The medicament delivery device of claim 9, wherein the second coupling comprises one or more radial recesses on an outer surface of the hub and one or more corresponding radial inwardly extending protrusions on an inner surface of the inner cap.

12. The medicament delivery device of claim 9, wherein the third coupling comprises a first thread, having a first pitch, on an inner surface of an inner cap and a corresponding second thread, having the first pitch, on an outer surface of the retainer member.

13. The medicament delivery device of claim 12, wherein the third coupling comprises a third thread, having a second pitch, on an inner surface of an inner cap and a corresponding fourth thread, having the second pitch, on an outer surface of the retainer member.

14. The medicament delivery device of claim 9, wherein the outer cap has at least one radial outwardly extending turning member.

15. The medicament delivery device of claim 9, wherein the delivery member is configured for operation in an unlocked mode,
   wherein the unlocked mode comprises the outer cap being rotatable in relation to the inner cap but incapable of moving the hub in a distal direction such that the needle cannot puncture the membrane.

16. The medicament delivery device of claim 9, wherein the delivery member is configured for operation in a locked mode,
  wherein the locked mode comprises locking the outer cap to the inner cap by moving the cap inter-locking member axially in a proximal direction such that the cap inter-locking member is coupled to the annular member on the inner surface of the outer cap.

17. The medicament delivery device of claim 9, wherein the deliver member is configured to operate in a primed mode,
  wherein the primed mode comprises the hub being moved in a distal direction such that the distal needle end punctures the membrane.

* * * * *